(12) United States Patent
Yamamoto et al.

(10) Patent No.: US 8,998,788 B2
(45) Date of Patent: Apr. 7, 2015

(54) APPARATUS AND METHOD FOR FOLDING ARTICLES

(75) Inventors: Yoichiro Yamamoto, Cologne (DE); Thomas Ludwig Woschnik, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 935 days.

(21) Appl. No.: 13/183,483

(22) Filed: Jul. 15, 2011

(65) Prior Publication Data
US 2012/0015790 A1    Jan. 19, 2012

Related U.S. Application Data

(60) Provisional application No. 61/364,610, filed on Jul. 15, 2010.

(51) Int. Cl.
| | |
|---|---|
| *B31F 1/10* | (2006.01) |
| *A61F 13/15* | (2006.01) |
| *B31F 1/00* | (2006.01) |
| *B65H 5/22* | (2006.01) |

(52) U.S. Cl.
CPC ......... *A61F 13/15747* (2013.01); *B31F 1/0019* (2013.01); *B65H 5/226* (2013.01)

(58) Field of Classification Search
CPC ........... B31F 1/10; B65B 25/20; B65B 63/04; A61F 13/15747; B65H 5/266; B65H 5/10; B65H 5/04; B65H 5/12
USPC ......... 493/442, 441, 356, 231, 416, 418, 424, 493/450, 435
See application file for complete search history.

(56) References Cited

U.S. PATENT DOCUMENTS

| | | | | |
|---|---|---|---|---|
| 4,521,209 | A | * | 6/1985 | DuFresne ..................... 493/432 |
| 4,767,487 | A | * | 8/1988 | Tomsovic, Jr. ................ 156/256 |
| 4,940,464 | A | | 7/1990 | Van Gompel et al. |
| 5,092,861 | A | | 3/1992 | Nomura et al. |
| 5,167,897 | A | | 12/1992 | Weber et al. |
| 5,246,433 | A | | 9/1993 | Hasse et al. |

(Continued)

FOREIGN PATENT DOCUMENTS

| | | |
|---|---|---|
| EP | 1 595 517 A1 | 11/2005 |
| EP | 1 726 278 A1 | 11/2006 |

(Continued)

OTHER PUBLICATIONS

PCT International Search Report dated Sep. 27, 2011, 10 pages.

(Continued)

*Primary Examiner* — Hemant M Desai
*Assistant Examiner* — Eduardo R Ferrero
(74) *Attorney, Agent, or Firm* — Sarah M. DeCristofaro; Abbey A. Lopez; John G. Powell

(57) ABSTRACT

An apparatus for folding articles advancing in a machine direction including a rotatable roll having a roll surface, at least one protrusion that defines an outermost surface of the roll and at least one pocket that defines an innermost surface of the roll. The apparatus also includes a peel assembly and a folding assembly. The peel assembly and/or folding assembly may be configured as one or more movable heads for receiving an article or article portion from a first carrier at a first speed and transferring the article to a second carrier travelling at a second speed.

19 Claims, 13 Drawing Sheets

(56) References Cited

U.S. PATENT DOCUMENTS

| | | | |
|---|---|---|---|
| 5,360,420 A | 11/1994 | Cook et al. | |
| 5,385,526 A * | 1/1995 | Sigrist et al. | 493/14 |
| 5,569,234 A | 10/1996 | Buell et al. | |
| 5,599,335 A | 2/1997 | Goldman et al. | |
| 5,643,588 A | 7/1997 | Roe et al. | |
| 5,674,216 A | 10/1997 | Buell et al. | |
| 5,702,551 A | 12/1997 | Huber et al. | |
| 5,897,545 A | 4/1999 | Kline et al. | |
| 5,957,908 A | 9/1999 | Kline et al. | |
| 5,968,025 A | 10/1999 | Roe et al. | |
| 6,107,537 A | 8/2000 | Elder et al. | |
| 6,118,041 A | 9/2000 | Roe et al. | |
| 6,120,487 A | 9/2000 | Ashton | |
| 6,120,489 A | 9/2000 | Johnson et al. | |
| 6,153,209 A | 11/2000 | Vega et al. | |
| 6,357,505 B1 * | 3/2002 | Jurgens | 156/564 |
| 6,410,129 B2 | 6/2002 | Zhang et al. | |
| 6,426,444 B2 | 7/2002 | Roe et al. | |
| 6,514,187 B2 * | 2/2003 | Coenen et al. | 493/418 |
| 6,586,652 B1 | 7/2003 | Roe et al. | |
| 6,617,016 B2 | 9/2003 | Zhang et al. | |
| 6,627,787 B1 * | 9/2003 | Roe et al. | 604/364 |
| 6,705,453 B2 | 3/2004 | Blumenthal et al. | |
| 6,723,035 B2 * | 4/2004 | Franklin et al. | 493/450 |
| 6,748,996 B2 * | 6/2004 | Nakakado et al. | 156/556 |
| 6,825,393 B2 | 11/2004 | Roe et al. | |
| 6,861,571 B1 | 3/2005 | Roe et al. | |
| 6,888,143 B2 | 5/2005 | Vogt et al. | |
| 7,399,266 B2 * | 7/2008 | Aiolfi et al. | 493/424 |
| 8,469,869 B2 * | 6/2013 | Yamamoto | 493/442 |
| 2002/0103468 A1 | 8/2002 | Nakakado et al. | |
| 2003/0233082 A1 | 12/2003 | Kline et al. | |
| 2004/0077474 A1 * | 4/2004 | Saraf et al. | 493/352 |
| 2007/0129230 A1 * | 6/2007 | Sosalla | 493/441 |
| 2008/0197164 A1 * | 8/2008 | Schmitz | 226/1 |
| 2009/0094941 A1 * | 4/2009 | Burns et al. | 53/429 |
| 2009/0098995 A1 * | 4/2009 | Burns et al. | 493/440 |
| 2009/0101687 A1 * | 4/2009 | Raueiser | 226/95 |
| 2012/0015790 A1 * | 1/2012 | Yamamoto et al. | 493/442 |
| 2012/0157286 A1 * | 6/2012 | Coenen et al. | 493/416 |

FOREIGN PATENT DOCUMENTS

| | | | | |
|---|---|---|---|---|
| EP | 1 941 854 A2 | 7/2008 | | |
| WO | WO 95/19752 A2 | 7/1995 | | |
| WO | WO 2008/001209 A2 | 1/2008 | | |
| WO | WO 2009/032995 A1 | 3/2009 | | |
| WO | WO 2009/083788 A1 | 7/2009 | | |
| WO | WO 2009083788 A1 * | 7/2009 | | A61F 13/15 |

OTHER PUBLICATIONS

PCT International Search Report dated Aug. 30, 2011, 11 pages.
U.S. Appl. No. 13/183,481, filed Jul. 15, 2011, Yoichiro Yamamoto.
U.S. Appl. No. 13/183,486, filed Jul. 15, 2011, Yoichiro Yamamoto.
U.S. Appl. No. 13/183,490, filed Jul. 15, 2011, Yoichiro Yamamoto.
U.S. Appl. No. 12/203,339, filed Sep. 3, 2008, John Glasgow Burns, Jr.
U.S. Appl. No. 13/051,210, filed Mar. 18, 2011, Yoichiro Yamamoto.

* cited by examiner

APPARATUS AND METHOD FOR FOLDING ARTICLES

CROSS REFERENCE TO RELATED APPLICATIONS

This application claims the benefit of U.S. Provisional Patent Application Ser. No. 61/364,610, filed Jul. 15, 2010, which is hereby incorporated by reference in its entirety.

FIELD OF THE INVENTION

The present disclosure relates to methods and apparatuses for manufacturing articles, and more particularly, to an improved transport roll and method for increasing the rate of article transport, especially during a folding operation.

BACKGROUND OF THE INVENTION

Disposable absorbent articles, such as diapers, pull-on diapers, training pants, adult incontinence pads, wipes, facial tissue, toilet tissue, napkins, paper towels, and the like are often manufactured and/or packaged on a high-speed production line where individual articles may move along a production path at a speed of hundreds of meters per minute, and manufacturers of articles are continually trying to increase manufacturing speed. However, in order to increase the speed of a manufacturing process, larger, more powerful drive motors are typically required to increase the operational speed of the various components in the process. Such motors can be costly and take up an undesirable amount of floor space in the manufacturing facility.

In conventional manufacturing processes, it is not uncommon for rolls, sometimes referred to as drums or cylinders, to be used to transport articles from one component or portion of the process to another (e.g., folding drums for bifolding an article). Known folding rolls and/or transport rolls typically have a substantially uniform, two-dimensional, curved surface. An article such as a disposable diaper disposed on the surface of a conventional roll is generally considered to be in a so-called "flat-out" configuration on the roll surface (i.e., no slack in the article which could cause bunching, wrinkles, looseness, or the like). Thus, the number of flat-out articles of a particular length that can be accommodated by a roll may be directly determined by the circumference of the roll. For example, a conventional folding drum having a circumference of 600 mm can accommodate no more than three articles having a length of 200 mm each, assuming the articles do not overlap one another. If the length of each article is increased, for example to 220 mm, and the circumference of the roll is unchanged, then only two articles can be accommodated by the roll per revolution, assuming articles do not overlap. Reducing the size of the articles, for example to 190 mm each, without changing the circumference of the roll may permit the same number of article to be processed, but in instances where the roll is "pitched" (i.e., sized and timed such that the articles are positioned on a particular portion of the roll) then it may be necessary to replace the roll. While it is possible to replace a roll, it may be expensive and time consuming. Increasing the speed of the roll may increase the rate at which articles are processed, but, as pointed out above, it typically requires providing a larger motor, which may not be desirable. In addition, if variable speed servo motors are used, increasing the size of the motor may increase the inertia of the motor and potentially offset the desired speed and/or acceleration benefits. Decreasing the size of an article may increase the rate at which the articles can be processed. But decreasing the size of an article may not be a practical option for certain articles such as disposable diapers, training pants, or other articles that are typically manufactured in particular sizes to fit different sizes of wearers.

Accordingly, it would be desirable to provide a process and apparatus for increasing the rate at which articles may be transported on a roll without increasing the size and/or rotational speed of the roll. It would also be desirable to provide a process and apparatus for folding articles and providing substantially aligned end and/or side edges on the folded articles without the use of a mechanical holding means.

SUMMARY OF THE INVENTION

At least one embodiment herein discloses an apparatus for folding articles advancing in a machine direction. Each article may have a leading end and a trailing end. The apparatus may comprise a rotatable roll comprising a roll surface and an article disposed thereon. The roll surface may include at least one protrusion and at least one pocket. The apparatus may include a peel assembly. The peel assembly may include one or more movable heads configured to rotate about an axis. The peel assembly may receive at least a portion of the leading end of the article from the rotating roll (230). The one or more movable heads each may be driven by a variable speed motor such that the movable heads each travel at a first speed when receiving the leading end of the article and then decelerate to second slower speed. The apparatus may include a folding assembly including a movable surface for engaging the leading end of the article and applying a peel force thereto such that at least a portion of the leading end of the article is transferred from the peel assembly to the movable surface of the folding assembly. The movable surface of the folding assembly may be driven by a variable speed motor such that the movable surface receives the leading end of the article from the peel assembly (245) while travelling at the second speed and then accelerates to the first speed while carrying the leading end of the article back to the rotating roll. The folding assembly may be configured to transfer the leading end back to the rotating roll such that the leading end and the trailing end are arranged in a face-to-face relationship to form a folded article.

DETAILED DESCRIPTION OF THE INVENTION

Definitions

Figure 1:
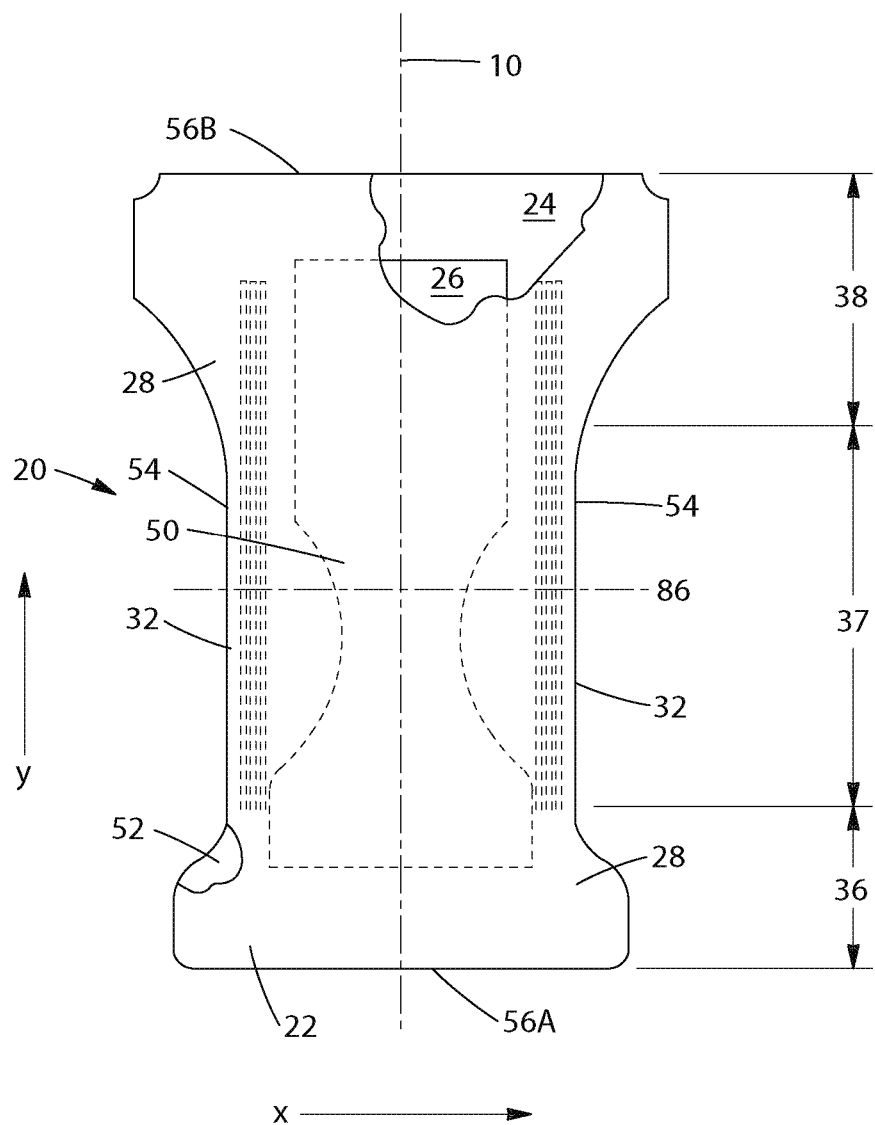
FIG. 1 is a top, plan view of a disposable absorbent article.

"Absorbent article" means a product whose primary function is to absorb and retain soils and wastes, such as devices which are placed against or in proximity to the body of the wearer to absorb and contain various exudates discharged from the body. Nonlimiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Aligned" means an article in a bifold configuration having an average CD accuracy and an MD accuracy of less than or equal to 3 mm, when measured according to the Alignment Test described in U.S. Patent Application Publication. No. 2009/0098995, titled "System For Bifolding An Absorbent Article," filed by Burns, et al.

"Bifold" means folding an article into two portions. For example, bifolding a disposable diaper may be accomplished by bringing the leading end and the trailing end of the diaper together in a face-to-face configuration on a production line as the article moves in the machine direction of travel, such that the diaper is folded along a fold line into two substantially equal portions. As used herein, a "fold line" is the portion of an article about which the article is folded. The fold line typically extends from one side edge to the opposing side edge in the crotch region and, in certain embodiments, may correspond to the lateral centerline of the article. In certain embodiments, the leading end edge and trailing end edge of an article may be aligned after the article is folded.

"Diaper" or "taped diaper" mean disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Suitable taped diapers are disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

"Disposable" means articles that are generally not intended to be laundered or otherwise restored or reused as absorbent articles (i.e., they are intended to be discarded after a single use and may be recycled, composted or otherwise discarded in an environmentally compatible manner).

"Disposed" means an element(s) is formed (joined and positioned) in a particular place or position as a macro-unitary structure with other elements or as a separate element joined to another element.

"Engage," when used in the context of transferring an article from one carrier to another or from a portion of one carrier to another portion of the same carrier, means coming into close proximity (e.g., less than 10 cm, up to and including physical contact) such that an engaging force (e.g., suction) present at the surface of the carrier can be applied to an article.

"Holding an article to the surface of a roll" and variations thereof mean employing a holding force to one or more portions of an article in order to join the article at least temporarily to the surface of a roll such that the article is inhibited from traveling in a direction substantially orthogonal to the surface of the roll without reducing or removing the holding force and/or employing a peel-force. This definition is equally applicable to conveyors, e.g., one or more of the conveyor assemblies described herein.

"Joined" means configurations whereby an element is directly secured to another element by affixing the element directly to the other element and to configurations whereby an element is indirectly secured to another element by affixing the element to intermediate member(s) which in turn are affixed to the other element.

"Longitudinal" means a direction running substantially perpendicular from a waist edge to an opposing waist edge of an absorbent article when the article is in a flat out, uncontracted state, or from a waist edge to the bottom of the crotch in a bifolded article. Directions within 45 degrees of the longitudinal direction are considered to be "longitudinal." "Lateral" refers to a direction running from a longitudinal edge to an opposing longitudinal edge of an article and generally orthogonal to the longitudinal direction. Directions within 45 degrees of the lateral direction are considered to be "lateral."

"Machine direction" ("MD") means the direction that is parallel to the direction of travel of an article or article element as it is processed in the forming apparatus. In a folding process such as a bifolding process, it may be possible to have more than one machine direction when an article is undergoing simultaneous processes. In other words, a manufacturing line may have an overall machine direction, but an article may travel in directions other than the overall machine direction as it passes through various process along the manufacturing line. For example, an article having a trailing end portion and a leading end portion, each portion being attached to the surface of a different roll and/or conveyor, may travel in two different directions simultaneously. In this example, both directions of travel may be considered the machine direction. The "cross machine direction" or "cross direction" ("CD") refers to the direction perpendicular to the machine direction and in the plane generally defined by the article or article element.

"Mechanically coupled" means two or more components that, directly or indirectly, act cooperatively to form a mechanism. For example, an electric motor that drives the motion of a gate is said to be mechanically coupled to the gate. The mechanism of operation that mechanically couples the component may be any one of a number of commonly known couplers, including but not limited to: having a shaft extending between the components; a universal joint; a transmission; a linkage; a sprocket and chain; a gear head on one of the components; a gear box; a belt and pulley combination; a clutch mechanism; a spring member; a slider; a pivot; or other known forms of coupling two elements may also be considered mechanical coupling.

"Mechanically secured" means holding an object in place by a mechanical means. For example, a web of material or an absorbent article held to the outer surface of a roll with clips is considered to be mechanically secured. Conversely, holding a web of material or an absorbent article to the surface of a roll with vacuum pressure or centrifugal force is not an example of being mechanically secured.

"Peel force" means the force applied to an object in a direction that is substantially perpendicular to the plane of the surface on which the object rests. A force applied in a direction within 45° of the perpendicular direction may be considered a peel force.

"Training pant(s)" or "pant(s)" mean disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by any suitable technique including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened, front waist fastened, rear waist fastened). Suitable examples of pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

"Vacuum" and "vacuum pressure" mean a pressure of less than 100,000 Newtons per square meter, and, in some embodiments, less than 13,000 Newtons per square meter.

For ease of understanding, portions of the following description may be exemplified in terms of a disposable absorbent article. However, it is to be understood that while one or more particular examples recited herein may refer to a diaper or training pant, the present invention is not limited to such articles. The folding assembly system described herein may, in fact, be practiced in any situation where an article exhibiting the characteristics described herein is required. Examples of other articles include hard surface cleaning wipes or pads; pre-moistened cloths; paper towels; dryer sheets and dry-cleaning cloths; adult incontinence briefs and undergarments; feminine hygiene garments such as panty liners, absorbent inserts, and the like; toilet paper; tissue paper; personal cleaning wipes or clothes such as baby wipes or facial wipes; packaging components and substrates and/or containers for laundry detergent and coffee, which may be produced in pellets or pouches and may be manufactured in a converting or web process; or even discreet products produced at high speed such as high-speed bottling lines, cosmetics, razor blade cartridges, and disposable consumer batteries.

FIG. 1 shows a partial cut-away view of a diaper 20 shown in a flat-out, uncontracted state (e.g., with no elastic induced contraction). The diaper 20 may include a body-faceable, liquid pervious topsheet 22 (i.e., faces and/or contacts the body of a wearer when worn as intended); a clothing-faceable, liquid impervious backsheet 24 joined with the topsheet 22 (i.e., faces and/or contacts the clothing of a wearer when worn as intended); an absorbent core 26 positioned between the topsheet 22 and the backsheet 24; side panels 28; and leg cuffs 32. The diaper 20 may further include an outer surface 52 opposed to the inner surface 50, a first waist region 36, a second waist region 38 opposed to the first waist region 36, and a crotch region 37 positioned between the first waist region 36 and the second waist region 38. The diaper 20 may also include longitudinal edges 54. As shown in FIG. 1, a first end edge 56A corresponds to the first waist region 36, and an opposing second end edge 56B corresponds to the second waist region 38. The diaper 20 may include a longitudinal centerline 10 positioned midway between the longitudinal side edges 54 and a lateral centerline 86 positioned midway between opposing end edges 56A and 56B and orthogonal thereto. The end edges 56A and 56B may be substantially equal in width, as measured from opposing longitudinal side edges 54 to the longitudinal centerline 10, or length, as measured from opposing end edges 56A and 56B to the lateral centerline 86, in order to facilitate folding of the diaper 20, but need not necessarily be so. According to the methods and apparatuses disclosed herein, the diaper 20 may be folded about the lateral centerline 86 such that the first waist region 36 and the second waist region 38 are positioned in a face-to-face relationship along the inner surface 50 (e.g., in a bifolded configuration). A folded diaper according to certain embodiments may have the first end edge 56A and the second end edge 56B aligned. A folded diaper according to certain embodiments may have the longitudinal side edges 54 partially or entirely aligned (e.g., the longitudinal side edges 54 may be aligned only in those areas that are visible to a consumer and/or are to be permanently joined together).

Figure 2:
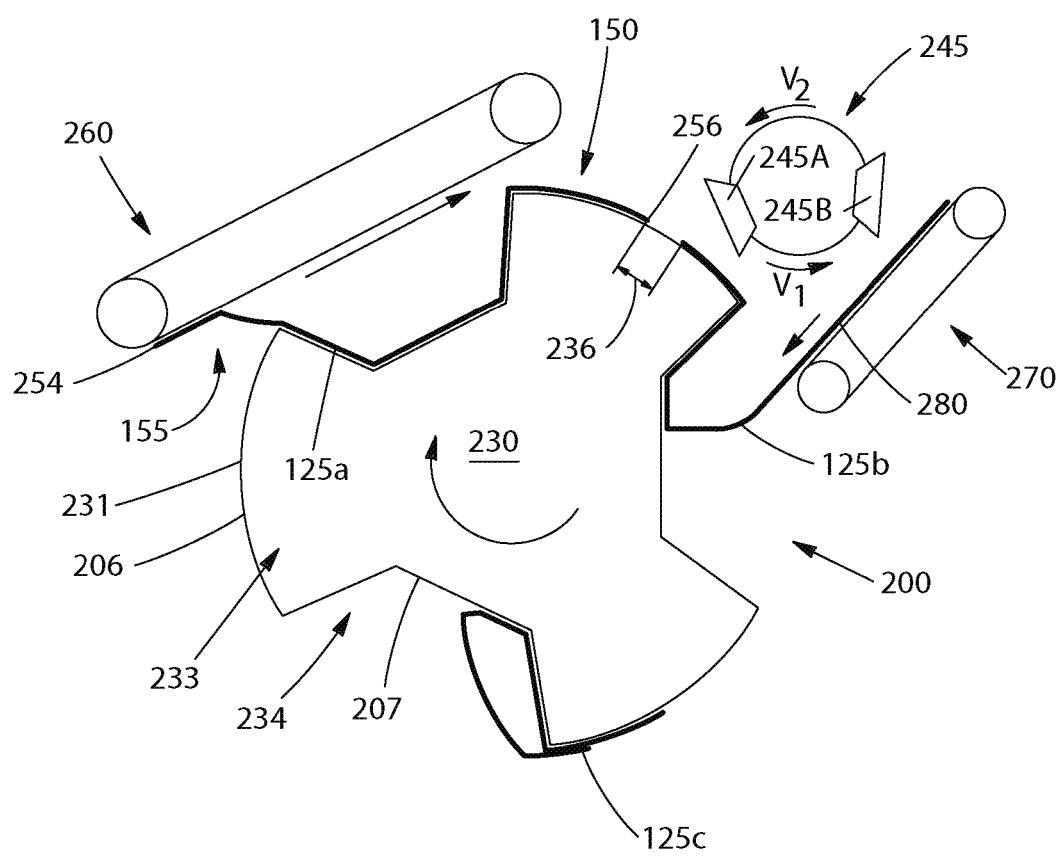
FIG. 2 is schematic side view of an embodiment of the apparatus and method disclosed herein.

FIG. 2 shows an exemplary embodiment of a folding apparatus 200 that includes a folding drum 230, a peel assembly 245, and a folding assembly 270. In certain embodiments, the folding drum 230 may be configured as a commonly known vacuum drum (i.e., drum that is configured to apply vacuum/suction at one or more portions of its surface). The surface 231 of the folding drum 230 is defined by an alternating series of pockets 234 and protrusions 233. Some or all of the pockets 234 and/or protrusions 233 may be extend the full width of the surface 231 of the folding drum 230 in the CD, such that the profile of the folding drum 230 appears "gear-like." In certain embodiments, some or all of the pockets 234 and/or protrusions 233 may extend only partially across the folding drum 230 in the CD. The protrusions 234 and/or pockets 233 may be configured to hold an article 125 (such as article 125a, article 125b, or article 125c) to the surface 231 of the folding drum, for example, with vacuum. Suitable folding drums 230 for use herein may include any number of protrusions 233 and/or pockets 234, as desired.

Figure 13:
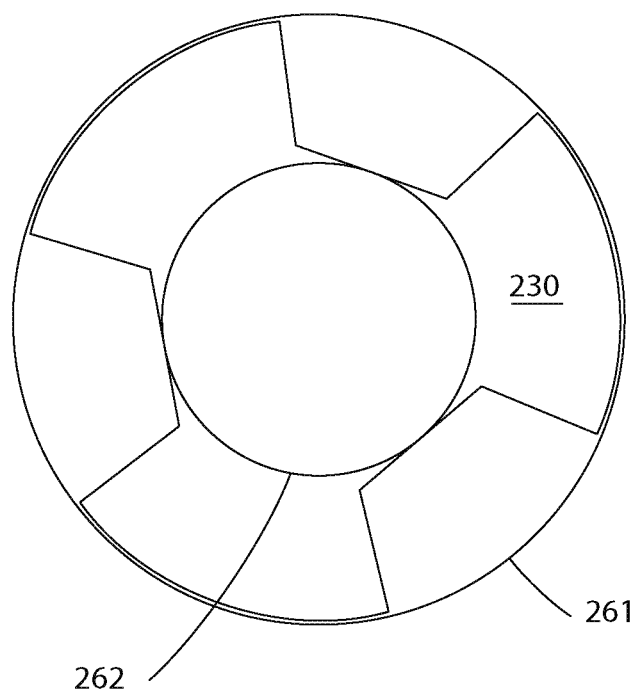
FIG. 13 is a schematic view of an embodiment of the apparatus and method disclosed herein.

It is to be understood that the terms protrusion 233 and pocket 234 are relative terms, which are used to conveniently describe the contrasting surface features of folding drum 230. The protrusions 233 and pockets 234 may be uniformly sized such that all the pockets are the same size and/or all of the protrusions are the same size. Alternatively, some or all the protrusions and/or pockets may be different sizes. Suitable examples of pockets sizes include a depth (i.e., the distance that the pocket 234 extends inwardly, orthogonally, from the outermost surface of a protrusion 233) of between 10 and 150 mm, 20 and 100 mm, 30 and 80 mm, or even 60 mm. While not particularly limited, the pockets may be sized according the article and/or portion of the article to be placed in the pocket. The protrusions 233 may define the outermost portion 206 of the surface 231 and the outer circumference 261 of the folding drum 230, as shown in FIG. 13, while the pockets 234 define an innermost portion 207 of the surface 231 and an inner circumference 262. The number of protrusions 233 and pockets 234 present on the folding drum 230 depends on the number of articles to be accommodated by the folding drum 230 (e.g., at least one pocket 234 and at least one protrusion 233 may be required for each article to be accommodated). The protrusions 233 and/or pockets 234 may have relatively uniform surfaces (e.g., smooth). But in certain embodiments, some or all of the pockets 234 and/or protrusions 233 may include surface features such as corrugations, fingers, channels, rough portions, smooth portions, raised portions, lowered portions and the like, for example, to aid in holding and/or transferring an article 125 to and/or from the surface 231 of the folding drum 230. Examples of additional surface features and/or other features known in the art, which may be suitable for use with the present folding drum 230, are disclosed in copending U.S. Ser. No. 12/203,339, filed Sep. 3, 2008 by Burns, et al., and 61/322,333, filed Apr. 9, 2010 by Yamamoto, et al. and titled "Apparatuses And Methods For Folding An Absorbent Article."

In certain embodiments (e.g., when the absorbent article 125 is in the form of a disposable diaper or pant), the absorbent article 125 may be transferred to the surface 231 of the folding drum 230 such that the topsheet of the absorbent article 125 is facing outward and the backsheet of the absorbent article 125 is held against the surface 231 of the folding drum 230. The absorbent article 125 may be oriented in relation to a predetermined path to provide a leading end portion 150 positioned downstream of a trailing end portion 155. The leading end 150 of the article 125 may be transferred from the transfer apparatus 260 to a protrusion 233 on the folding drum 230. For example, as the folding drum 230 rotates and a protrusion 233 becomes positioned proximate to the transfer apparatus 260, the leading end 150 of the absorbent article 125 may be transferred to the protrusion 233 (e.g., by applying a peel force to the leading end 150). After the leading end 150 is transferred to the protrusion 233, a holding force (e.g., vacuum) may be applied to the leading end 150 to secure it to the surface 231 of the folding drum 230. In certain embodiments, one or more portions of the article 125 (e.g., the middle portion) may be mechanically secured to the surface 231 of the folding drum 230, for example, with movable bifold clamps such as those described in copending U.S. Ser. Nos. 12/203,339 and 61/322,333. As the folding drum 230 continues to rotate, the absorbent article 125 continues to be transferred from the transfer apparatus 260 to the folding drum 230 until the entire absorbent article 125 has been transferred to the folding drum 230. The absorbent article 125 may be disposed on the folding drum 230 such that a first portion of the article (e.g., the leading end portion 150) is disposed on a first protrusion 233 ("leading protrusion"), the middle portion of the absorbent article 125 is disposed in the pocket 234 adjacent the leading protrusion, and a third portion of the disposable article (e.g., the trailing end portion 155) is disposed on a second protrusion 233 ("trailing protrusion"). In certain embodiments, it may be desirable to provide at least some slack in the article 125 to facilitate transferring a portion of the article 125 (e.g., the middle portion) to the pocket 234. For example, if an article is transferred to the folding drum with no slack, as in a conventional process (i.e., in an extended flat out configuration), the article may be stretched over the pocket 234 like a cover, instead of being placed within the pocket 234. However, it is to be understood that, in certain embodiments, a portion of an article in a flat-out configuration may be placed in a pocket 234 by positioning the transfer apparatus closer to the inner surface 207 of the pocket 234 and/or providing sufficient vacuum at the inner surface 207 of the pocket 234 to pull the article portion into the pocket 234. Further, the holding force exerted by transfer apparatus may be reduced, removed, or even reversed (e.g., from negative pressure to positive pressure) to facilitate placement of the article portion within the pocket 234. Still further, a portion of the article 125 may be transferred to the pocket 234 mechanically, for example, by using hooks; loops; pistons; clips; clamps; fingers, pins; combinations of these and the like or any other suitable mechanical transfer means known in the art. Since the folding drum 230 typically rotates continuously, a leading protrusion may include both the leading end 150 of one article and the trailing end 155 of the preceding article 125 in the process. Thus, it may be desirable to provide a suitable space 236 between the trailing end edge 254 of a first absorbent article 125b and the leading end edge 256 of the following absorbent article 125a (e.g., between 1 and 200 mm apart; 2 and 100 mm; 5 and 80 mm; or even between 10 and 50 mm), which are disposed on the same protrusion 233, as shown in FIG. 2. In certain embodiments, the transfer apparatus 260 may be configured to provide suitable spacing between the articles 225. Examples of a suitable transfer apparatus may be found in copending U.S. Ser. No. 61/364,626, titled Method and Apparatus For Transferring Articles of Different Sizes, filed Jul. 15, 2010, by Yamamoto, et al. as U.S. Pat. No. 6,705,453 to Blumenthal, et al., on Mar. 16, 2004.

After the article 125 is transferred to the folding drum 230, the leading end 150 of the article 125, which is disposed on a protrusion 233, may be carried toward the peel assembly 245 at a first speed $V_1$. The peel assembly 245 may have one or more heads 245A, 245B configured to travel in an orbital path around an axis at two or more different speeds, as described in more detail below. The folding drum 230 and the peel assembly 245 may be positioned to provide a suitable distance between the surface 231 of the folding drum 230 and the movable heads 245A, 245B of the peel assembly 245 such that an article 125 disposed on the surface 231 of the folding drum 230 can pass by the peel assembly 245 with little or no resistance. For example, as the trailing end 155 of the article 125 approaches the peel assembly 245, the trailing end 155 may pass by without contacting the heads 245A, 245B, or even come into contact with the heads 245A, 245B, as long as the contact does not substantially impede the advancement of the absorbent article 125 in the MD. In certain embodiments, the peel assembly 245 may be configured to peel or remove at least a portion of the leading end 150 of the absorbent article 125 from the outer surface 231 of the folding drum 230 at the first speed $V_1$ (i.e., the speed at which the leading end 150 is travelling) and slow the leading end 150 to a second speed $V_2$ (i.e., $V_2<V_1$).

The peel assembly 245 may be configured to transfer the leading end 150 to the folding assembly 270 at the second speed $V_2$. In certain embodiments, the speed and/or direction of the movable surface 280 of the folding assembly 270 may be adjusted to match the speed and/or direction of the heads 245A, 245B of the peel assembly 245 when the leading end 150 is transferred. For example, the movable surface 280 of the folding assembly 270 may be travelling in the same direction (i.e., away from the folding drum 230) and at substantially the same speed (e.g., within 1%, 2%, 3%, 4%, or even 5%) as the movable surface 232 of the peel assembly 245. In this example, after the leading end 150 is transferred to the folding assembly 270, the direction and/or speed of the movable surface 280 of the folding assembly 270 may be changed (e.g., sped up) such that the leading end 150 is carried back toward the folding drum at the first speed $V_1$. The folding assembly 270 may be configured as a vacuum conveyor 270 with a belt 280 travelling in an endless loop. The folding drum 230 and the folding assembly 270 may be positioned to provide a suitable distance between the surface 231 of the folding drum 230 and the movable surface 280 of the folding assembly 270 such that an article 125 disposed on the surface 231 of the folding drum 230 can pass by the folding conveyor surface 280 with little or no resistance. The folding assembly 270 may be configured to accelerate the leading end 150 back to the first speed $V_1$ and transfer the leading end 150 back to the folding drum 230. In this way, the leading end 150 and the trailing end 155 may be traveling at substantially the same speed when the two portions 150, 155 are brought together in a face-to-face relationship to provide a folded article 125c. The folded article 125c may then be subjected to one or more additional, optional processes such as a commonly known process for permanently and/or refastenably joining the front and back side panels of the article 125 to one another to form a disposable pant or a pre-fastened disposable pant. Exemplary methods for seaming, inspecting, and tucking an article to form a pre-fastened pant are disclosed in U.S. Pat. No. 6,888,143, issued to Vogt, et al.

Figure 3A:
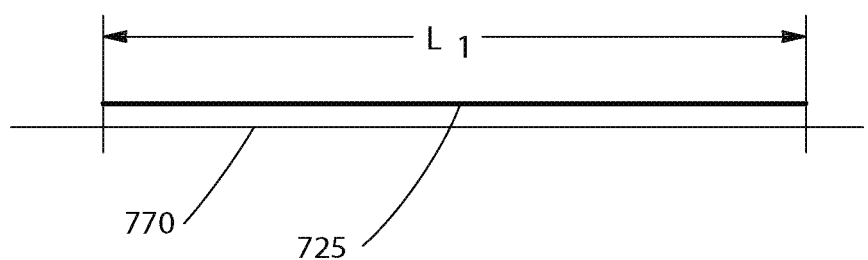
FIGS. 3A and 3B are cross-section views of an article supported on a surface.
Figure 3B:
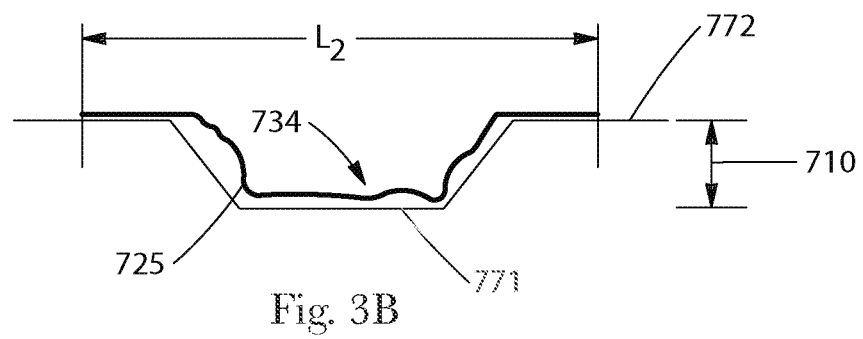

By providing a folding drum 230 with pockets 234, a portion of the absorbent article 125 (e.g., the middle portion)

may be desirably positioned in the pocket 234, thereby reducing the distance between the leading end edge 256 and the trailing end edge 254 and effectively reducing the length of the article 125. Thus, the length of an article can be adjusted to match the pitch of the drum, which may eliminate the need to replace the drum when manufacturing articles of different lengths. FIGS. 3A and 3B illustrate how placing a portion of an article in a pocket may reduce the overall length of the article being supported on a surface. FIG. 3A shows an article 725 disposed on a flat surface 770. The article 725 has a length $L_1$, which is disposed entirely on the flat surface 770. FIG. 3B shows the article 725 of FIG. 3A disposed on a surface 771 that includes a pocket 734 having a depth 710. As can be seen in FIG. 3B, part of the article 725 is disposed on an outer surface portion 772 and part of the article 725 is disposed in the pocket 734 on the inner surface portion 771. Thus, the length $L_2$ of the article 725 disposed on the outer surface 772 shown in FIG. 3B is less than the length $L_1$ of the article disposed on the surface 770 shown in FIG. 3A, by up to two times the depth 710 of the pocket 734 or more. For example, if the pocket has a depth of 60 mm, the length $L_2$ of the article 725 supported on the outer surface 772 may be approximately 120 mm less than the length $L_1$ of the article disposed on the flat surface 770.

Although FIGS. 3A and 3B show slack in article 725 roughly coincident with the surface length of the pocket 734, it should be understood that other embodiments may have slack in article 725 in excess of the surface length of the pocket 734, or may the surface length of the pocket 734 may exceed the slack in article 725 (i.e., article 725 may not lie against all or even most of the surface of pocket 734. As described above, in some embodiments, inner surface portion 771 is not smooth or linear, but may be curvilinear or shaped. Fingers or other protrusions from the inner surface portion 771 may be configured, for example, to hold a shorter article (or shorter length of article slack) in a relatively larger pocket 734, or to prevent article 725 from resting against the entire surface length of inner surface portion 771. In some embodiments, a pocket 734 sized to allow article 725 to lie substantially against the surface length of inner surface portion 771 may help to prevent wrinkles from forming in the article, or reduce the number or depth of the wrinkles formed in the article, while it is folded.

Figure 4:
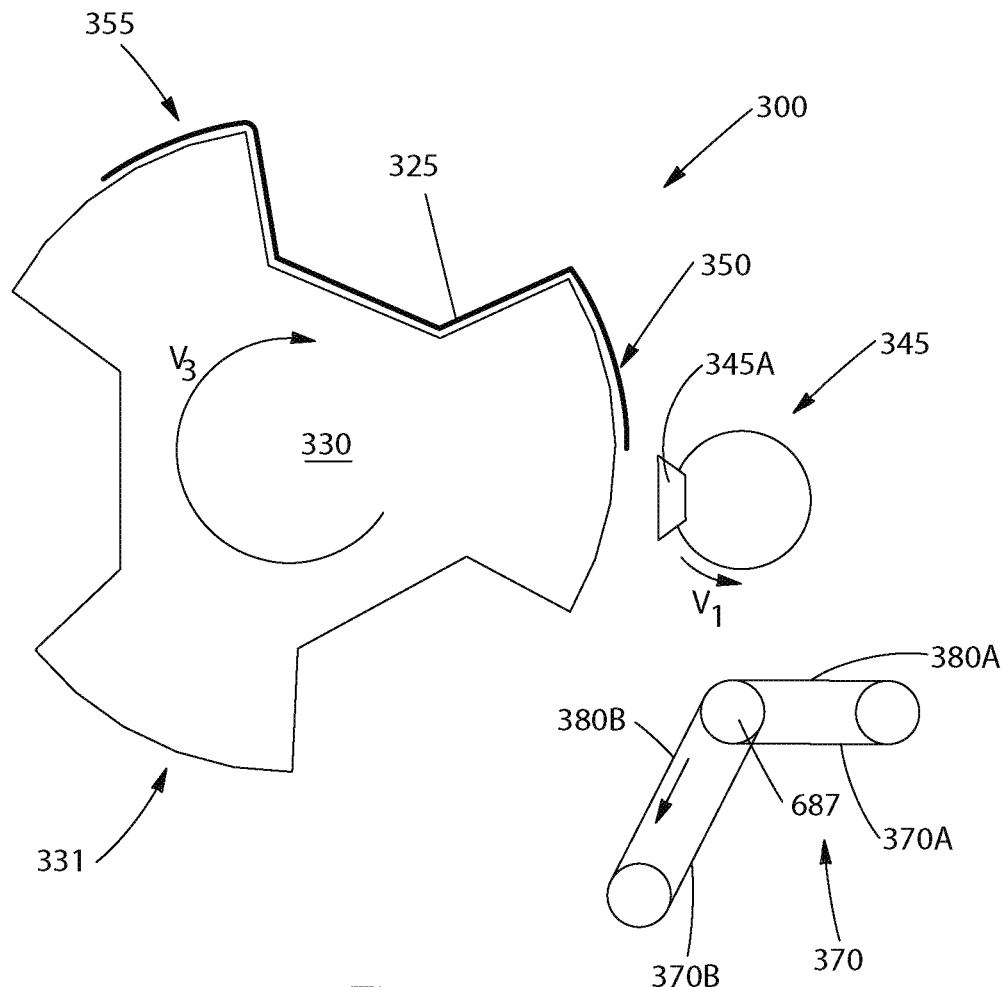
FIG. 4 is a schematic side view of an embodiment of the apparatus and method disclosed herein.

FIG. 4 shows an exemplary embodiment of a folding system 300 that includes a rotatable folding drum 330, a peel assembly 345 and a folding assembly 370. The folding drum 330 may be configured as one or more of the folding drums described herein. The folding drum 330 includes a surface 331 for carrying an article 325. As shown in FIG. 4, the peel assembly 345 includes a movable head 345A. For ease of explanation, FIG. 4 shows the peel assembly 345 as having only one movable head 345A, but it is to be understood that the peel drum 345 may include two or more movable heads, as desired. The peel assembly 345 may be configured as a drum having a stationary surface over which the movable heads travel. Alternatively or additionally, the peel assembly 345 may be configured such that the movable heads 345A form rib-like structures whose length is substantially parallel to the axis about with they rotate. In such an embodiment, the peel assembly 345 may not have a surface other than that formed by the movable heads 345A. The movable head 345A of the peel assembly 345 may be configured to exert vacuum on an article 325 or article portion disposed on the surface of the movable head 345A. In certain embodiments, the movable head 345A may be configured to travel a full 360° in one or both directions (i.e., clockwise and/or counterclockwise). In other embodiments, the movable head 345A may be configured to travel only partway around the circumference of its orbital path (i.e., less than 360°) in one or both directions. In certain embodiments, the movable head 345A may be configured to move at two or more speeds. For example, the movable head 345A may be configured to travel at the same speed or substantially the same speed as the leading end 350 (i.e., $V_1$) and at one or more slower second speeds ($V_2$), including a speed of zero.

Figure 5:
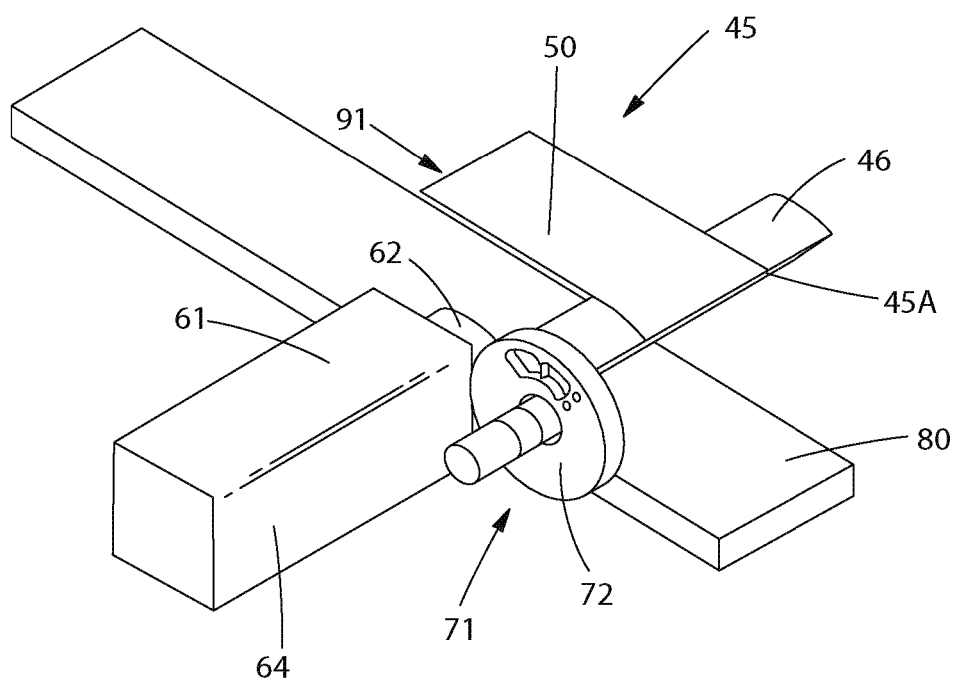
FIG. 5 is a perspective view of an embodiment of a peel assembly.
Figure 6:
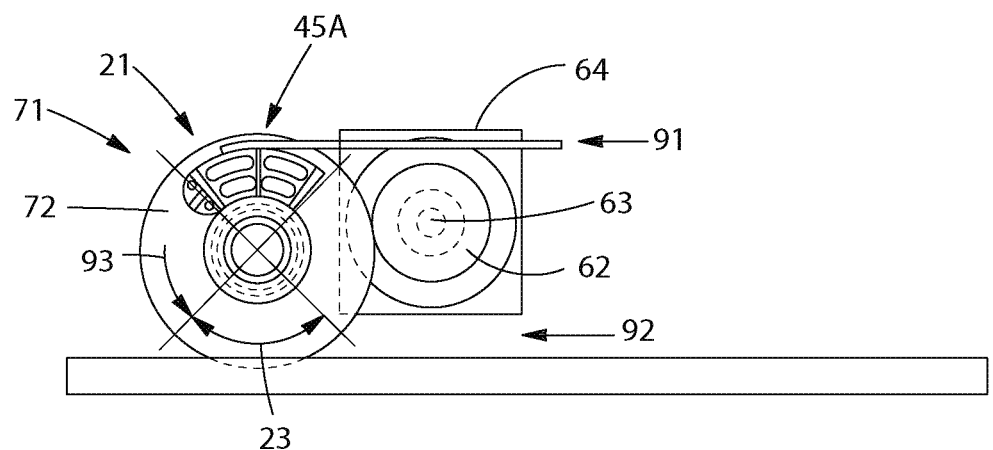
FIG. 6 is schematic side view of the peel assembly of FIG. 5.

FIGS. 5 and 6 show an exemplary embodiment of a peel assembly 45 suitable for use herein. In certain embodiments, the peel assembly 45 receives, for example, the leading end 50 of an article traveling at a first speed in the direction indicated by the arrow 91 from a first carrier (e.g., folding drum) and transfers the leading end 50 to a second carrier 80 (e.g., folding assembly) traveling at a second speed. The movable head 45A may be configured to apply a peel force (e.g., vacuum) to the leading end 50 to at least help transfer (e.g., peel) the leading end 50 from the first carrier and/or secure the leading end 50 to the surface 46 of the movable head 45A. The peel assembly 45 may include a drive mechanism 61 for transmitting rotational energy to a driven mechanism 71. The drive mechanism 61 may be mechanically coupled to the driven mechanism 71 by any suitable technique known to those skilled in the art such as, for example, gear to gear connection, transmission belting and pulleys, gearboxes, direct couplings, and the like or any combinations thereof. For example, the drive mechanism 61 may be connected to a drive gear 62 which transmits rotational energy to a driven gear 72 connected to the driven mechanism 71. In use, the drive gear 62 engages and rotates the driven gear 72 which, in turn, rotates the movable head 45A. The dimensions of the movable head 45A may vary depending upon the size and/or shape of the article being folded. For example, the outer surface 46 of the movable head 45A may be defined by a crescent-shaped outer, peripheral arc length spanning from about 5 degrees to about 340 degrees, an outer radius ranging from about 25 mm to about 500 mm, and a width ranging from about 50 mm to about 750 mm.

As shown in FIG. 6, the driven mechanism 71 rotates to move the movable head 45A in the direction indicated by the arrow 92. The circumferential, outer surface 46 of the movable head 45A travels along and defines an orbital path that passes through a receiving zone 21 and an application zone 23. The receiving zone 21 and the application zone 23 are defined by the respective regions of the orbital path traveled by the movable head 45A. In certain embodiments, the drive mechanism 61 may include a rotatable circular drive gear 62 connected to an input shaft 63. In this example, the input shaft 63 is the output shaft of the motor 64. The driven mechanism 71 may be positioned parallel to the drive mechanism 61 such that the drive gear 62 meshes with the driven gear 72 using gear set-ups known to those skilled in the art. In use, the motor 64 rotates the input shaft 63 which rotates the drive gear 62 which, in turn, rotates the driven gear 72 and movable head 45A. The driven mechanism 71 may include any mechanism known to those skilled in the art by which rotational energy can be conducted from one shaft to another such as, for example, v-belts, timing belts, continuous chains and the like or combinations thereof. Further, the driven mechanism 71 may include any mechanism known to those skilled in the art by which input velocity can be variably modified to an output source such as, for example, cams, linkages, and the like or combinations thereof as long as the changes in rotational speed are substantially created by the motor 64.

Figure 7:
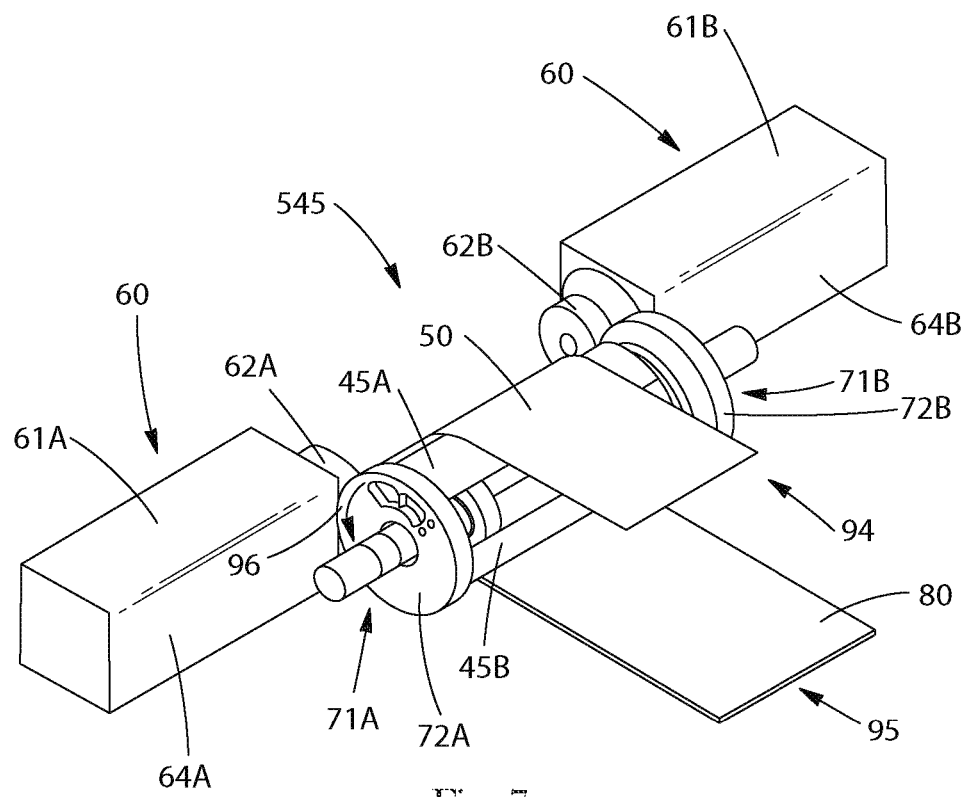
FIG. 7 is a perspective view of an embodiment of a peel assembly disclosed herein.

FIG. 7 shows an exemplary peel assembly 545 receiving a leading end portion 50 traveling at a first speed in the direction indicated by the arrow 94 associated therewith and applies the parts to a carrier 80 traveling at a second speed in the direction indicated by the arrow 95 associated therewith. In this example, the peel assembly 545 includes two rotatable heads 45A, 45B for receiving and transferring the leading end 50. The peel assembly 545 further comprises a driving system 60 having two driving mechanisms 61A and 61B, each of which includes a motor 64A, 64B and a driving gear 62A, 62B for transmitting rotational energy to the driven mechanism 71A, 71B represented by the driven gear 72A, 72B. As illustrated in FIG. 7, each movable head 45A, 45B may be connected to a driven gear 72A, 72B. As each gear rotates, the movable heads 45A, 45B travel in the direction indicated by the arrow 96 associated therewith. In use, the circumferential, outer peripheral surface of the movable heads 45A, 45B travels along and defines an orbital path that passes through a receiving zone and an application zone defined by the respective regions of the orbital path traveled by the movable heads 45A, 45B. The size and shape of the movable heads 45A, 45B may vary as the number of movable heads 45A, 45B changes. For example, if the peel assembly includes two transferring devices as representatively illustrated in FIG. 7, each movable head 45A, 45B may have an outer peripheral arc length which spans from about 5 to about 175 degrees of the orbital path. Each driven mechanism 71A, 71B may include any mechanism known to those skilled in the art by which rotational energy can be conducted from one shaft to another such as, for example, v-belts, timing belts, continuous chains and the like or combinations thereof. In certain embodiments, a first driven mechanism may connect to a first transferring device using a first shaft from a driven gear, and a second driven mechanism may be connected to a second transferring device using concentric shafting around the first shaft.

For receiving the parts in the receiving zone, the peel assembly may be configured to apply a peel force and/or a holding force to the leading end of an article being folded and/or transferred. For example, the outer surface of one or more of the movable heads may include ports or holes to selectively impose vacuum at the outer surface. In this example, the vacuum may be activated in the receiving zone to seize the parts and reduced and/or deactivated in the application zone to release the parts to a carrier. In this manner, positive control is maintained over the parts at all times during the transfer process. In certain embodiments, peel and/or holding force may be provided by any technique known to those skilled in the art for gripping and releasing parts such as, mechanical clamps, electrical clamps, magnetic clamps and the like or combinations thereof. In certain embodiments, the peel assembly may include a programmable motor (e.g., servo motor) to vary the speed of the movable head as it travels between the first and second carriers. Suitable examples of programmable motors, control systems for such motors, and techniques for programming the control systems are disclosed in U.S. Pat. No. 6,705,453 to Blumenthal, et al.

Referring again to FIG. 4, the folding assembly 370 may include a first folding conveyor 370A and a second folding conveyor 370B. The first and second folding conveyor 370A, 370B may each include a movable surface 380A, 380B for receiving an article from the peel assembly 345 and securely carrying it back toward the folding drum 330. In certain embodiments, the first and second folding conveyors 370A, 370B may share one or more common elements such as, for example, a shaft 687. Shaft 687 may be coupled to, e.g., a variable speed drive motor and configured to drive the endless belt 380A of the first folding conveyor 370A at one or more speeds. The shaft 687 may also include one or more freespinning rollers or pulley-like elements that enable the shaft 687 to simultaneously operate as an idler roll for the endless belt 380B of the second folding conveyor 370B. The second folding conveyor 370B may be driven by, e.g., a constant speed motor that drives the second folding conveyor belt 380B at, e.g., the surface speed of the folding drum 330, through a mechanical coupling. By sharing shaft 687, the first and second folding conveyor belts 380A, 380B may be configured to overlap at one end in the machine direction, and thereby facilitate transfer of an article from the first folding conveyor 370A to the second folding conveyor 370B. While the first and second folding conveyors 370A, 370B may share a common element, it is to be understood that the first and second folding conveyors 370A, 370B may also be configured as discrete components. It is also to be appreciated that, in certain embodiments, the second conveyor 370B may also be configured as a variable speed conveyor.

Figure 8:
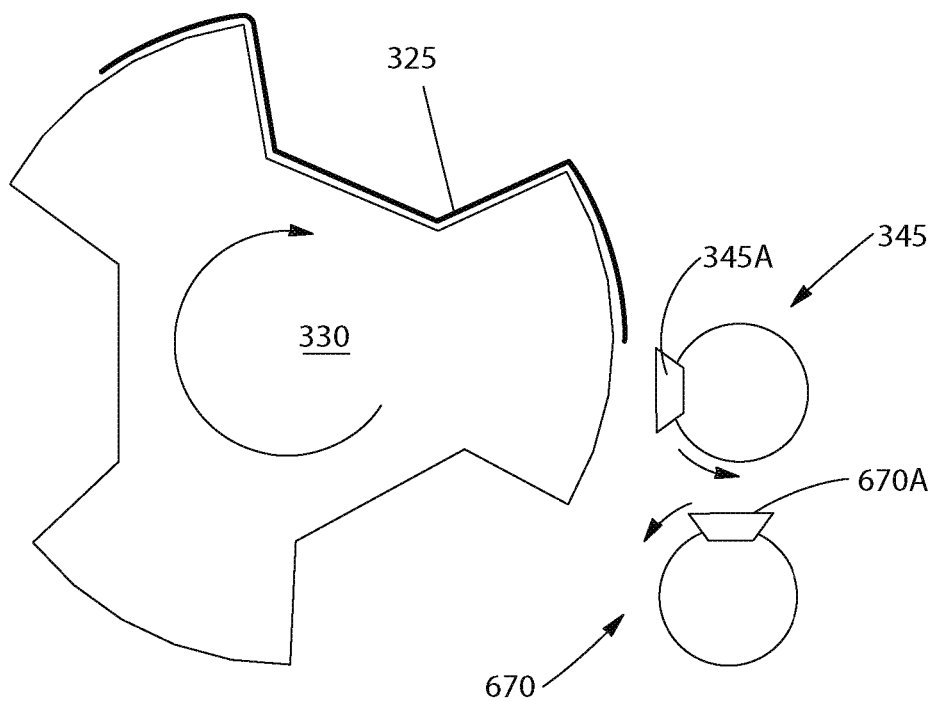
FIG. 8 is a schematic side view of an embodiment of the apparatus and method disclosed herein.

In certain embodiments, the folding assembly 670 may be configured to include movable heads in addition to or in place of a conveyor, as illustrated in FIG. 8. As illustrated in FIG. 8, the folding assembly 670 may include one or movable heads 670A configured to receive the leading end of an article 325 from the peel assembly 345 and transfer it back to the folding drum 330. The movable head(s) 670A of the folding assembly 670 may be configured as one or more of the exemplary embodiments described above with regard to the peel assembly 45, 545. In certain embodiments, the peel assembly 345 may include one or more conveyors configured to transfer a portion of an article to the movable head 670A of the folding assembly 670, in addition to or in place of the movable heads 345A.

Figure 9:
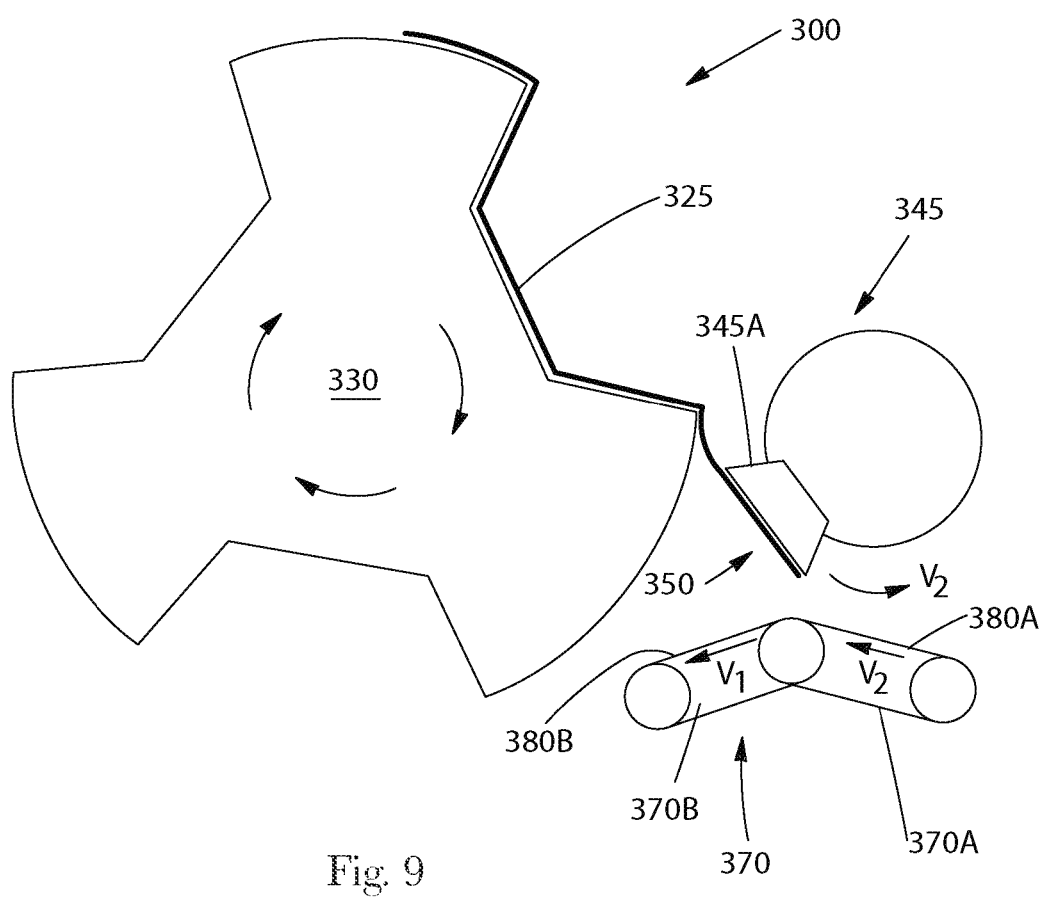
FIGS. 9-12 are schematic side views of an embodiment of the apparatus and method disclosed herein.

Referring to FIGS. 4 and 9-12, an exemplary process for folding an article with the folding system 300 is described. As shown in FIG. 4, the folding drum 330 rotates to position the leading end 350 of the article 325 proximate the peel assembly 345 at speed $V_1$. Thus, in certain embodiments, it may be desirable to configure the movable head 345A to travel at speed $V_1$, e.g., within 0.5%, 0.2%, 0.1%, or even identical to the surface speed of the folding drum 330. As the leading end 350 of the article 325 approaches the peel assembly 345, at least a portion of the leading end 350 may be transferred and secured to the movable head 345A, as shown in FIG. 9. Any force exerted by the folding drum 330 on the leading end 350 (e.g., vacuum and/or mechanical) may be simultaneously or sequentially removed or reduced as the leading end 350 is peeled from the folding drum 330. After receiving the leading end 350 of the absorbent article 325 from the folding drum 330, the movable head 345A decelerates the leading end 350 to speed $V_2$ (i.e., speed $V_2<V_1$), and transports the leading end 350 towards the movable surface 380A of the first folding conveyor 370A and transfers it thereto. At the time of transfer, the speed of the first folding conveyor 370A may substantially match the speed of the movable head 345A (e.g., speed $V_2$). Upon engaging the leading end 350, the folding assembly 370 may be configured to apply sufficient peel force (e.g., suction) to the leading end 350 to overcome the holding force of the peel assembly 345. In certain embodiments, it may be desirable to reduce or remove the holding force exerted by the peel assembly 345 on the absorbent article 325 or portions thereof when the absorbent article 325 reaches a desired position or when the folding assembly 370 engages the leading end 350.

In certain embodiments, the first folding conveyor surface 380A may be traveling in substantially the opposite direction as the movable head 345A. Thus, in order to reduce the possibility of premature engagement or contact between the movable head 345A and/or leading end 350 and the first folding conveyor, a suitable distance or gap may be provided between the movable head 345A and the first folding conveyor surface 380A. In certain embodiments, one or both of the movable surfaces 380A, 380B of the folding assembly 370 may be repositionable relative to the peel assembly 345 and/or folding drum 330 via a positioning mechanism mechanically coupled to the folding assembly 370. Similarly, in certain embodiments, the peel assembly 345 may be repositionable relative to the folding assembly 370 and/or folding drum 330 via a positioning mechanism mechanically coupled to the peel assembly 345. A suitable positioning mechanism may be configured to automatically vary the distance between the first movable surface 380A of the folding assembly 370 and the movable head 345A of the peel assembly 345 in a continuous or intermittent fashion. Such positioning mechanisms may include for example, one or more cams, pistons, gears, pulleys, and the like. The positioning mechanism may be configured to suitably position the first folding conveyor 370A to engage the leading end 350 during the "upstroke" (i.e., when the movable surface 380A of the first vacuum conveyor 370A is being moved closer to the movable head 345A) and to provide a suitable gap between the vacuum conveyor 380A and the peel conveyor 345 during the "downstroke" (i.e., when the movable surface 380A of the first vacuum conveyor 370A is being moved away from the movable head 345A), as suitably exemplified in copending U.S. Ser. No. 61/322,333. The positioning mechanism may have any suitable stroke length desired, for example, a stroke length of greater than 1 mm, between 1 mm and 20 cm, 1 mm and 20 mm, 1 mm and 10 mm, or even 1 mm and 5 mm, which provide a gap distance that is at least greater than the thickness of the absorbent article 325, for example, greater than 1 mm, between 1 mm and 20 cm, or even between 1 mm and 20 mm. One particularly suitable example for providing a gap includes using a cam with a 3 mm stroke length to continuously vary the position of the first folding conveyor surface 380A relative to the moving head 345A. In certain embodiments, it may be desirable to vary or hold constant the distance between the surface 331 of the folding drum 330 and one or more of the movable conveyor surfaces 380A, 380B and/or the movable head 345A. In certain embodiments, the movement of the first folding conveyor 370A may pause at a particular position during the bifold process, for example, at the "top of the upstroke" (i.e., when the distance between the first folding conveyor surface 380A and the movable head 345A is at a minimum), the "bottom of the downstroke" (i.e., when the distance between the first folding conveyor surface 380A and the movable head 345A is at a maximum), and/or upon engaging the leading end 350. In a particularly suitable embodiment, the first folding conveyor 370A may pause at the top of the upstroke while simultaneously engaging the leading end 350.

Figure 10:
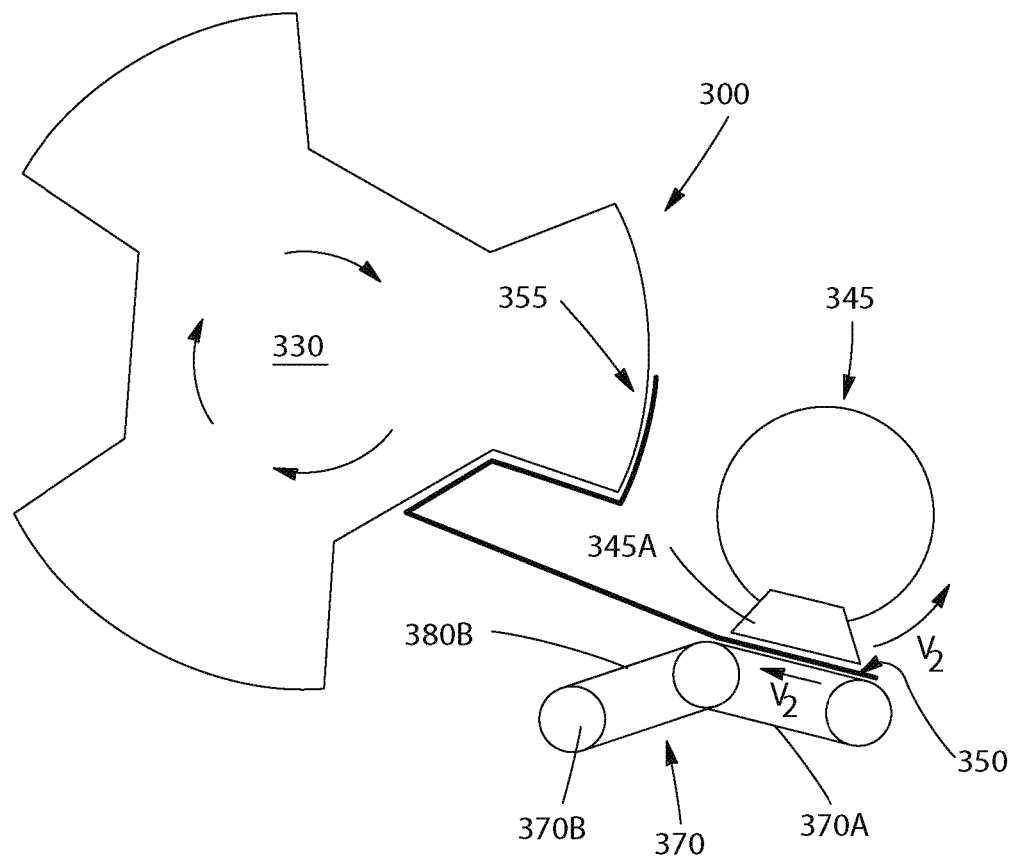
Figure 11:
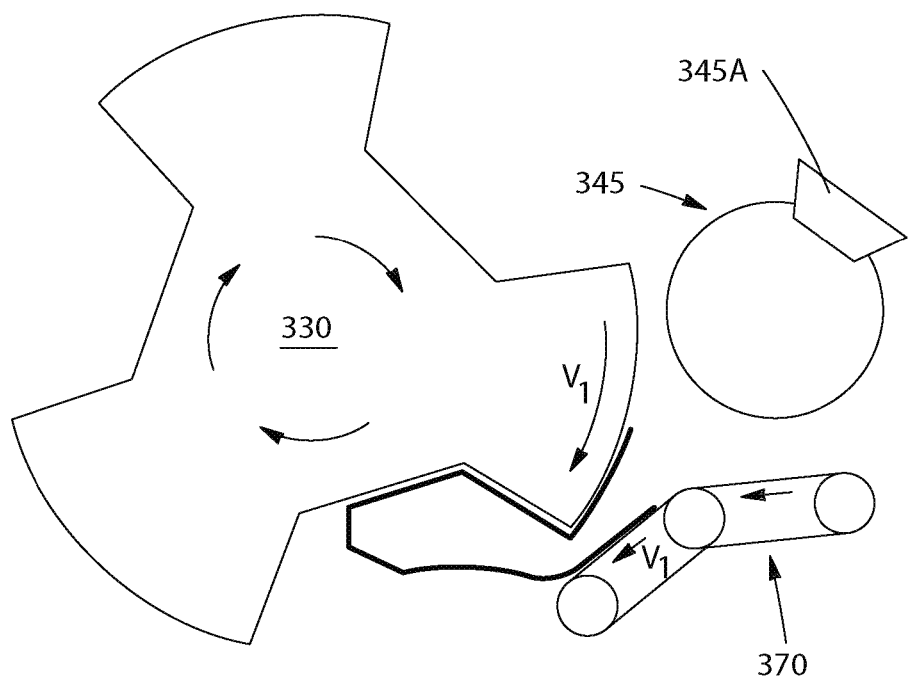
Figure 12:
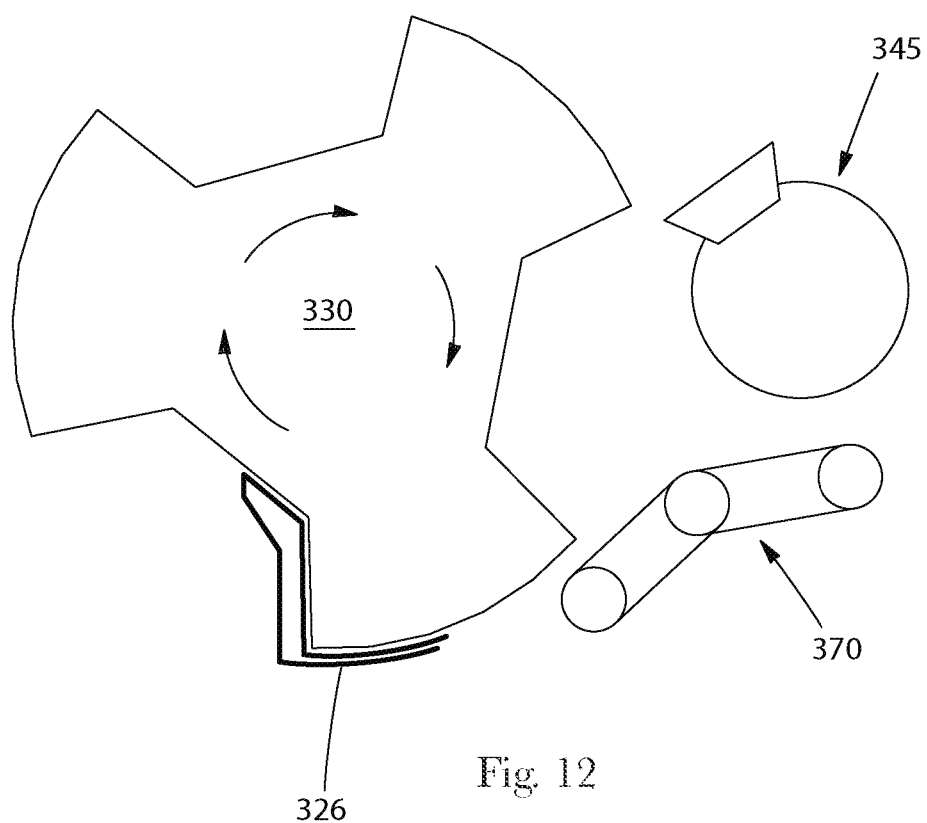

As illustrated in FIG. 10, once the leading end 350 has been transferred to the folding assembly 370 at the second speed $V_2$, the folding assembly 370 accelerates the leading end 350 back to the first speed $V_1$ and carries it back towards the folding drum 330 to be placed in a face-to-face relationship with the trailing end portion 355. The leading end 350 may then be transferred to the moving surface 380B of the second folding conveyor 370B, which is moving at the first speed $V_1$ toward the folding drum 330, as shown in FIG. 11. As shown in FIG. 12, the leading end 350 is transferred from the second folding conveyor 380B back to the folding drum 330 to provide a folded article 326, which can then be subjected to additional, optional processes such as adhesive and/or high pressure bonding or pre-fastening, for example, to form a pant product.

Figure 14:
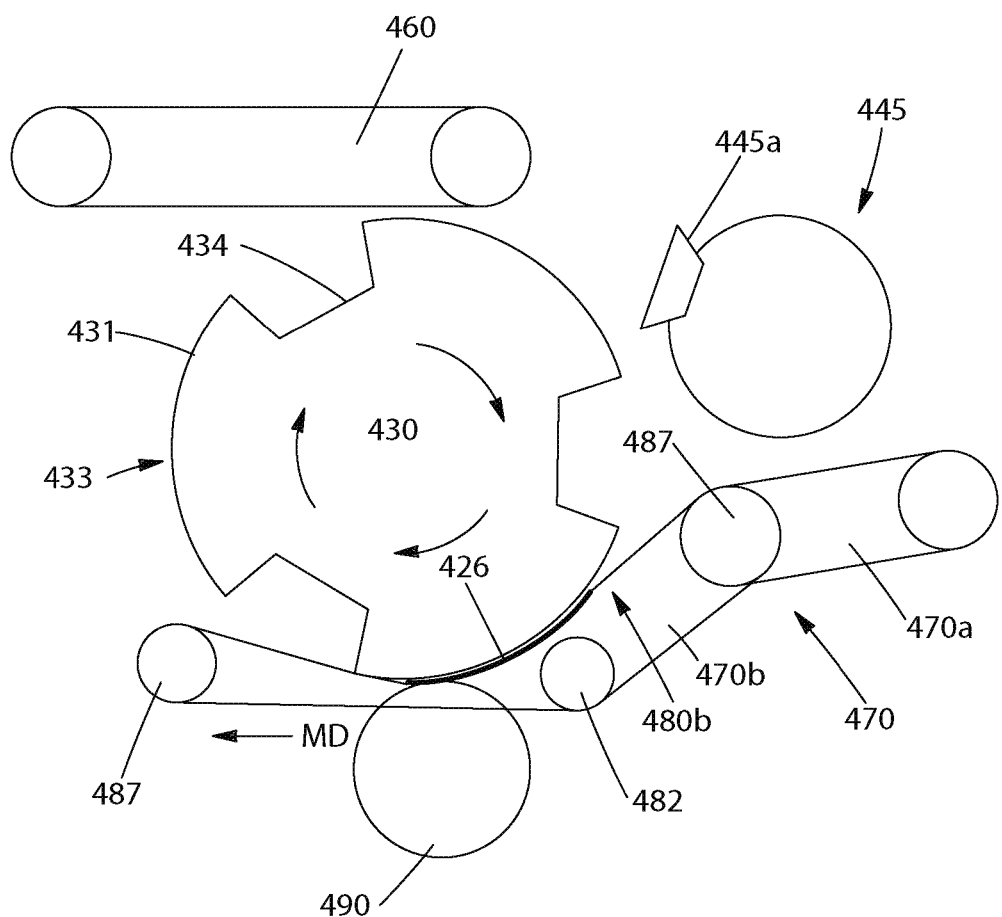
FIG. 14 is schematic view of an embodiment of the apparatus and method disclosed herein.

FIG. 14 shows an exemplary embodiment of a folding system that includes a rotatable folding drum 430, a peel assembly 445 and a folding assembly 470. The folding drum 430 includes a surface 431 defined by alternating pockets 434 and protrusions 433. An article may be fed to the folding system via a transfer apparatus 460 such as one or more of the transfer apparatuses described herein. The article may be carried around the surface 431 of the folding drum 430 toward the peel assembly 445 and the folding assembly 470 as the folding drum 430 rotates. The peel assembly 445 and folding assembly 470 may each be configured to include a single vacuum conveyor belt, two or more vacuum conveyor belts, or one or more movable heads. As shown in FIG. 14, the peel assembly 445 includes a movable head 445A, and the folding system includes first and second folding conveyors 470A, 470B. The first folding conveyor 470A may be configured to receive the leading end portion of a disposable absorbent article from the peel assembly 445 and transport it to the second folding conveyor, as described above. The first and second folding conveyors 470a, 470b may share a common element such as shaft 487 to facilitate transfer of an article or article portion. The second folding conveyor 470B receives the article portion and transports it toward the folding drum 430. As the folding drum 430 rotates, the leading and trailing end of an article disposed on the drum surface 431 are brought together in a face-to-face relationship to form a folded article 426. As shown in FIG. 14, the movable surface 480b of the second folding conveyor 470b may be extended to transport the folded article 426 to one or more downstream process such as a seaming process 490. As the folded article 426 advances in the MD, it may be disposed between the movable surface 480b of the second folding conveyor 470b and the surface 431 of the folding drum 430. In this way, the folded article 426 and/or article components may be less likely to shift position prior to reaching the seaming station 490. The second folding conveyor 470b may include one or more idler rolls 482 to help control the tension in the extended belt 480b, and may be driven by one or more constant or variable speed drive motors 487.

Although the figures show a flat article being folded, the process and apparatus described herein may be used to fold articles which have previously been folded in the CD. For example, longitudinal edges 54 may be folded back on themselves to form a finished edge around the leg opening of a diaper, or an article may be folded in the CD and then folded again in the MD to present a differently shaped or sized product (as folded). In some embodiments, the apparatus may comprise two or more like units to fold the article twice or more in the MD, e.g., to quad-fold the article, into even quarters or into another proportion. It should be understood that sequential units may require different apparatus component sizes, process speeds, or process forces to perform sequential folds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for folding articles advancing in a machine direction wherein each article has a leading end and a trailing end, the apparatus comprising:
 a rotatable roll comprising a roll surface and an article disposed thereon, the roll surface including at least one protrusion and at least one pocket, wherein at least a portion of the leading end of the article is disposed on a protrusion, and wherein the roll is configured to apply vacuum at least a portion of the roll surface which is sufficient to hold at least a portion of the article to the surface of the roll;
 a peel assembly including one or more movable heads configured to rotate about an axis and receive at least a portion of the leading end of the article from the rotating roll, the one or more movable heads each being driven by a variable speed motor such that the movable heads each travel at a first speed when receiving the leading end of the article and then slow down to a second slower speed; and
 a folding assembly including a movable surface for engaging the leading end of the article and applying a peel force thereto such that at least a portion of the leading end of the article is transferred from the peel assembly to the movable surface of the folding assembly, the movable surface of the folding assembly being driven by a variable speed motor such that the movable surface receives the leading end of the article from the peel assembly and then speeds up to the first speed while carrying the leading end of the article back to the rotating roll, the folding assembly being configured to transfer the leading end back to the rotating roll such that the leading end and the trailing end are arranged in a face-to-face relationship to form a folded article.

2. The apparatus of claim 1, wherein the rotatable roll is travelling at the first speed.

3. The apparatus of claim 1, further comprising a positioning mechanism mechanically coupled to the movable surface of the folding assembly such that a distance between the movable surface of the folding assembly and the movable head of the peel assembly can be varied.

4. The apparatus of claim 3, wherein the distance between the movable surface of the folding assembly and the movable head of the peel assembly is varied between 1 mm and 20 cm.

5. The apparatus of claim 3, wherein the positioning mechanism comprises a continuously operating cam for varying the distance between the movable surface of the folding assembly and the movable head of the peel assembly.

6. The apparatus of claim 3, wherein the positioning mechanism will alternatively position the moveable surface in an upstroke position and in a downstroke position, wherein in the upstroke position the moveable surface of the folding assembly engages the leading end of the article and in the downstroke position the moveable surface of the folding assembly is positioned to form a gap with the moveable head of the peel assembly.

7. The apparatus of claim 1, wherein the article includes a middle portion of the article disposed between the leading end and the trailing end and at least a portion of the middle portion is disposed within a pocket.

8. The apparatus of claim 1, wherein the folded article is a bifolded article.

9. The apparatus of claim 1, wherein the article is a disposable absorbent article comprising a first waist region and an opposing second waist region, and wherein at least one of the first and second waist regions include one or more side panels.

10. The apparatus of claim 1, wherein vacuum is present at the movable head such that a peel force is applied to the leading end portion of the article that is sufficient to transfer the first portion from the surface of the roll to the movable head of the peel assembly.

11. The apparatus of claim 1, wherein the article is disposable absorbent article comprising a body-faceable topsheet and a clothing faceable backsheet, and the backsheet is disposed on the surface of the roll.

12. The apparatus of claim 1, wherein the folding assembly includes first and second conveyors, each conveyor including a movable surface, the first conveyor movable surface configured to receive the leading end of the article from the peel assembly at the second speed and accelerate the leading end to the first faster speed, the first conveyor carrying the leading end to the second conveyor and the second conveyor carrying the leading end back to the roll at the first speed.

13. An apparatus for folding articles advancing in a machine direction wherein each article has a leading end portion and a trailing end portion, the apparatus comprising:
 a rotatable roll rotating at a first speed, the rotating roll comprising a roll surface and an article disposed thereon, the roll surface including at least one protrusion and at least one pocket, wherein at least a portion of the leading end of the article is disposed on a protrusion, and wherein the roll is configured to apply vacuum at least a portion of the roll surface which is sufficient to hold at least a portion of the article to the surface of the roll;
 a peel assembly including a movable head configured to rotate about an axis and receive at least a portion of the leading end of the article from the rotating roll, the movable head being driven by a variable speed motor such that the movable heads each travel at a first speed when receiving the leading end of the article and then slow down to a second slower speed; and
 a folding assembly including one or more movable heads configured to rotate about an axis and receive at least a portion of the leading end of the article from the peel assembly, the movable head being driven by a variable speed motor such that the movable head receives the leading end of the article from the peel assembly and then speeds up to the first faster speed while carrying the leading end of the article back to the rotating roll, the folding assembly being configured to transfer the leading end back to the rotating roll such that the leading end and the trailing end are arranged in a face-to-face relationship to form a folded article.

14. The apparatus of claim 13, wherein the vacuum at the surface of the roll is removed when the leading end is transferred to the movable head of the peel assembly.

15. The apparatus of claim 13, wherein the folding assembly and the peel assembly are both travelling at the second speed when the leading end is transferred from the peel assembly to the folding assembly.

16. The apparatus of claim 15, wherein the second speed is zero.

17. The apparatus of claim 13, wherein the folding assembly and the peel assembly are both travelling in the same direction when the leading end is transferred from the peel assembly to the folding assembly.

18. The apparatus of claim 13, wherein vacuum is selectively present at the movable heads of the peel assembly and folding assembly such that a peel force is applied to the leading end portion by the peel assembly and the folding assembly when the leading end portion is being received by the peel assembly or folding assembly.

19. The apparatus of claim 13, wherein at least one of the peel assembly movable head and the folding assembly movable head is driven by a programmable motor.

* * * * *